US012731667B2

(12) United States Patent
Ohri et al.

(10) Patent No.: US 12,731,667 B2
(45) Date of Patent: Sep. 8, 2026

(54) SYSTEM AND METHOD FOR SEAMLESS PRESCRIPTION MEDICATION DISCOUNTING

(71) Applicants: Shawn Ohri, Chula Vista, CA (US); Nathan Daugherty, Lake Villa, IL (US); Rajasekar Ramaswamy, San Diego, CA (US); Byung Joon Min, Dallas, TX (US)

(72) Inventors: Shawn Ohri, Chula Vista, CA (US); Nathan Daugherty, Lake Villa, IL (US); Rajasekar Ramaswamy, San Diego, CA (US); Byung Joon Min, Dallas, TX (US)

( * ) Notice: Subject to any disclaimer, the term of this patent is extended or adjusted under 35 U.S.C. 154(b) by 50 days.

(21) Appl. No.: 18/891,765

(22) Filed: Sep. 20, 2024

(65) Prior Publication Data

US 2026/0088147 A1 Mar. 26, 2026

(51) Int. Cl.
*G16H 20/10* (2018.01)
*G06Q 30/0207* (2023.01)

(52) U.S. Cl.
CPC ......... *G16H 20/10* (2018.01); *G06Q 30/0224* (2013.01)

(58) Field of Classification Search
CPC ........................... G16H 20/10; G06Q 30/0224
See application file for complete search history.

(56) References Cited

U.S. PATENT DOCUMENTS 10,430,555 B1 * 10/2019 Pinsonneault, Sr. ... G16H 20/10
10,496,793 B1 * 12/2019 Lawrence ............. G16H 40/20
2015/0095052 A1 * 4/2015 Weinstein ............. G16H 70/40 705/2
2015/0371000 A1 * 12/2015 Pinsonneault ......... G16H 10/60 705/2
2016/0358293 A1 * 12/2016 Berger ............... G06Q 30/0207
2016/0358294 A1 * 12/2016 Berger .................. G16H 20/10
2017/0344724 A1 * 11/2017 Nockley ................ G06Q 10/10
2021/0057072 A1 * 2/2021 Nockley ................ G07F 9/002
2022/0028513 A1 * 1/2022 Gangaikondan-Iyer .................... G06Q 30/04
2022/0285001 A1 * 9/2022 Jacobs .................. G06Q 40/08

(Continued)

OTHER PUBLICATIONS

F. S. Shaikh and R. Wismüller, "Routing in Multi-Hop Cellular Device-to-Device (D2D) Networks: A Survey," in IEEE Communications Surveys & Tutorials, vol. 20, No. 4, pp. 2622-2657, Fourthquarter 2018, doi: 10.1109/COMST.2018.2848108. (Year: 2018).*

(Continued)

*Primary Examiner* — Sun M Li

(74) *Attorney, Agent, or Firm* — Offit Kurman; Mary K. Nicholes

(57) ABSTRACT

A system and method for a seamless provision of discounting for prescription services that are not eligible for financial coverage by a plan, such as a Medicare Part D plan. The system and method take denials from Pharmacy Benefit Managers (PBMs) and seamlessly provides to end users (patients) a discounted cost for the denied coverage of the prescription. Denials of coverage are transmitted to a switch server where rejection codes are detected at the switch server and relayed to the seamless server. The seamless server then provides an approval instead of the original PBM.

20 Claims, 4 Drawing Sheets

(56) References Cited

U.S. PATENT DOCUMENTS

| | | | | |
|---|---|---|---|---|
| 2023/0281654 A1* | 9/2023 | Snopek | G16H 20/10 | |
| | | | 705/14.32 | |
| 2024/0153013 A1* | 5/2024 | Greenblatt | G16H 20/10 | |

OTHER PUBLICATIONS

Resource Management in Cloud Networking Using Economic Analysis and Pricing Models: A Survey by Nguyen Cong Luong, Ping Wang, Dusit Niyato, Wen Yonggang, and Zhu Han, arXiv:1701.01963v1 [cs.GT] Jan. 8, 2017 (Year: 2017).* https://www.fda.gov/downloads/ForIndustry/UserFees/PrescriptionDrugUserFee/UCM361087.htm, The TIRF REMS Access Program: Chain Pharmacy Enrollment Form, Jul. 1, 2013, FDA, pp. 1-3 (Year: 2013) (Year: 2013).*

J. Soldatos, E. Vayias and G. Kormentzas, "On the building blocks of quality of service in heterogeneous IP networks," in IEEE Communications Surveys & Tutorials, vol. 7, No. 1, pp. 69-88, First Qtr. 2005, doi: 10.1109/COMST.2005.1423335. (Year: 2005).*

Resource Management in Cloud Networking Using Economic Analysis and Pricing Models: A Survey by Nguyen Cong Luong, Ping Wang, Dusit Niyato, Wen Yonggang, and Zhu Han, arXiv:1701.01963v1 [cs.GT] Jan. 8, 2017 (Year: 2017) (Year: 2017).*

H. Yu, A. A. Irissappane, H. Wang and W. J. Lloyd, "FaaSRank: Learning to Schedule Functions in Serverless Platforms," 2021 IEEE International Conference on Autonomic Computing and Self-Organizing Systems (ACSOS), Washington, DC, USA, 2021, pp. 31-40, doi: 10.1109/ACSOS52086.2021.00023. (Year: 2021).*

* cited by examiner

SYSTEM AND METHOD FOR SEAMLESS PRESCRIPTION MEDICATION DISCOUNTING

TECHNICAL FIELD

This application relates to a system and method for distributing medication and, in particular, to seamless medication discounting.

BACKGROUND

Pharmacy Benefit Managers (PBMs) act as intermediaries between insurers, pharmacies, and drug manufacturers, managing prescription drug benefits for health insurers, Medicare Part D plans, large employers, and other payers. Their key functions include formulary management, where they develop and maintain lists of covered medications. This involves determining preferred drugs and their tiers, which impacts patient copayments and access. PBMs also negotiate drug prices, securing discounts and rebates from manufacturers based on purchase volumes, and negotiating dispensing fees with pharmacies.

Additionally, PBMs process prescription drug claims, ensuring whether they are covered according to health plan terms. PBMs also implement utilization management programs to control drug use, such as prior authorization, step therapy, and quantity limits. Through strategies such as generic substitution and therapeutic interchange, PBMs aim to manage drug utilization and to control costs for both health plans and patients.

The relationship between pharmacies and PBMs involves contractual agreements that outline reimbursement rates and dispensing terms. Pharmacies are reimbursed by PBMs for medications dispensed, while PBMs receive rebates from drug manufacturers. This arrangement influences access to medications and their out-of-pocket costs.

In summary, pharmacies and PBMs form the core infrastructure to the medication distribution and management system. They work together to provide medications to patients, navigating complex financial and operational dynamics to balance cost control with patient access and care quality.

There are times when the medication is not approved by the PBM. This usually results in the patient not receiving their medication and the pharmacy not receiving any payment for the prescription since the provision of the prescription is denied. Therefore, there is a need to provide a method and system to capture those denied sales of medical prescriptions and to provide approval for the initially denied sales of medical prescriptions.

SUMMARY

The method and system are directed towards seamless provision of access to discount server.

An aspect of the present disclosure is a method for seamless provision of discount prescription information. The method comprising transmitting prescription data from a pharmacy server to a switch server; transmitting the prescription data from the switch server to a pharmacy benefit manager (PBM) server; determining at the PBM server if financial coverage will be provided based on the prescription data; transmitting a rejection code to the switch server if it is determined that coverage will not be provided; processing the rejection code at the switch server to determine if the rejection code corresponds to an actionable rejection code; transmitting the rejection code from the switch server to the seamless server based on the processing of the rejection code; transmitting from the seamless server to the switch server destination information for sending the patient information and the medication information, wherein the destination information is at least one discount server; routing the patient information and the medication information to the discount server from the switch server; determining confirmation of coverage at the discount server using the patient information and the medication information; transmitting from the discount server to the switch server confirmation of coverage; and transmitting from the switch server to the pharmacy server the confirmation of coverage.

Another aspect of the disclosure is a system for seamless provision of discount prescription information. The system comprising a pharmacy server adapted to receive and transmit prescription data; a switch server operably connected to the pharmacy server, wherein the switch server is adapted to receive and transmit prescription data; a pharmacy benefit manager (PBM) server adapted to receive prescription data; wherein the PBM server is adapted to process prescription data to determine if financial coverage will be provided and if financial coverage will not be provided to generate a rejection code based in part on the prescription data; a seamless server adapted to receive processed rejection codes that are rejection codes received by the switch server and processed by the switch server to determine if the received rejections are actionable rejection codes, wherein the seamless server is adapted to transmit destination data related to a discount server to the switch server based on received processed rejection codes; and a discount server adapted to provide confirmation of coverage to the switch server based on patient information and medication information provided by the seamless server.

BRIEF DESCRIPTION OF THE DRAWINGS

The foregoing summary, as well as the following detailed description of illustrative embodiments of the present application, will be better understood when read in conjunction with the appended drawings. Illustrating the present application are the drawings that depict the embodiments of the disclosure. It should be understood, however, that the application is not limited to the precise arrangements and instrumentalities shown in the drawings.

DETAILED DESCRIPTION OF ILLUSTRATIVE EMBODIMENTS

Figure 1:
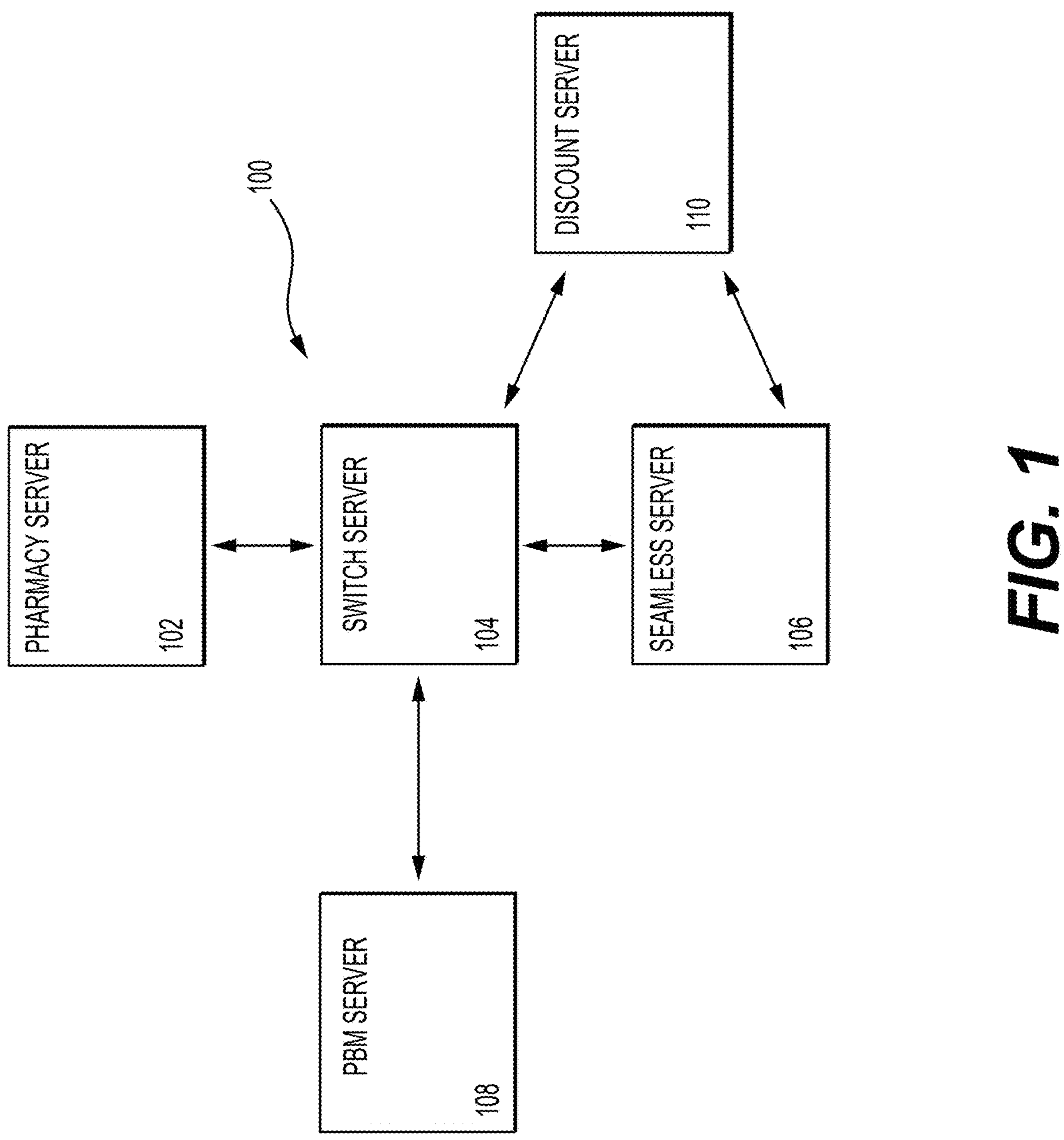
FIG. 1 shows a diagram of the system.

To facilitate an understanding of embodiments, principles, and features of the present disclosure, they are disclosed hereinafter with reference to implementation in illustrative embodiments. Embodiments of the present disclosure, however, are not limited to use in the described systems or methods and may be utilized in other systems and methods as will be understood by those skilled in the art.

The components described hereinafter as making up the various embodiments are intended to be illustrative and not restrictive. Many suitable components that would perform the same or a similar function as the components described herein are intended to be embraced within the scope of embodiments of the present disclosure.

The following detailed description refers to the accompanying drawings. Wherever possible, the same reference numbers are used in the drawings and the following description to refer to the same or similar elements. While embodiments may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the claimed subject matter. Instead, the proper scope of the claimed subject matter is defined by the appended claims.

Generally, the system and method seamlessly convert eligible rejected financial claims, such as Medicare Part D claims, to discount pricing, also known as Cash Discount Card (CDC) pricing and delivers the cash price back to the pharmacy. The seamless prescription discounting (SPD) system 100 provides real-time delivery of CDC pricing for claims rejected by an applicable patient's financial plan, such as a Medicare Part D benefit plan. The SPD system 100 provides automatic submission of claims based on qualified and configurable eligibility criteria.

Referring to FIG. 1, shown is diagram of the SPD system 100. The SPD system 100 comprises a pharmacy server 102, a switch server 104, a seamless server 106, a PBM server 108, and a discount server 110. The seamless prescription discounting (SPD) system 100 comprises the pharmacy server 102, switch server 104, seamless server 106, PBM server 108 and discount server 110 communicating the above-described data, and may exist in a separate server, and/or in software enhancements to the pharmacy server 102, switch server 104, seamless server 106, switch server 104, PBM server 108 and discount server 110, or otherwise.

The SPD system 100 is adapted to seamlessly provide reduced cost medication to people who are denied coverage by their financial plan, such as a Medicare Part D benefit plan. The SPD system 100 determines when a rejection code is received by the switch server 104 from the PBM server 108. The switch server 104 determines if the rejection code meets certain criteria. If the rejection code meets certain criteria, the switch server 104 then accesses the seamless server 106 to obtain information to route the coverage request to a discount server 110. The discount server 110 then provides a cost, CDC pricing, for the prescription to the switch server 104 that then relays the cost to the pharmacy server 102. The seamless server 110 can determine from available discount servers 110 which discount server 110 provides the lowest cost, any and all other variables being equal. This information is then conveyed to the switch server 104. The switch server 104 then provides the data for the lowest cost along with processing information BIN/PCN/Group data to the pharmacy server 102. In an embodiment, in a scenario wherein more than one discount server 110 provides the cost information, priority information can be associated with certain discount servers 110 to determine which discount server 110 should be utilized. In an embodiment, the discount servers 110 can have a predetermined rank to overcome situations where more than two discount servers 110 offer the same cost. This results in a seamless transaction from the perspective of the person obtaining the prescription.

Pharmacy server 102 is comprised of the computers, software, and applications that are implemented at a location where prescriptions can be fulfilled. Generally, the pharmacy server 102 stores and manages information related to the needs of a pharmacy. The pharmacy server 102 can be a physical server, or one of many servers, located onsite at the pharmacy. The pharmacy server 102 may be a cloud-based server. This pharmacy server 102 is adapted to manage patient prescriptions, track medication inventory, store patient information, process insurance claims, process financial coverage and ensure adherence to data privacy regulations. In the SPD system 100, the pharmacy server 102 receives prescription data. Prescription data can include, but is not limited to, insurance information, financial coverage information, patient information, and medication information.

The switch server 104 comprises computers, software, and applications that are implemented to relay information to other servers in the SPD system 100. The switch server 104 is further adapted to take data received from the PBM server 108 and determine if there are rejection codes. Once the determination of rejection codes is made, the switch server 104 can determine if the rejection codes are rejection codes identified by the seamless server 106 as being eligible for further processing.

The seamless server 106 comprises computers, software, and applications that are implemented to determine whether a discount server 110 will accept the rejection codes received from the switch server 104 for further processing. If the seamless server 106 determines that the rejection code will be accepted by a discount server 110, the seamless server 106 will transmit this information to the switch server 104 and the switch server 104 will transmit the patient information and medication information to the discount server 110.

The PBM server 108 comprises computers, software, and applications that are implemented to determine whether a selected prescription is eligible for financial coverage by a plan such as an individual's Medicare Part D benefit plan. The PBM server 108 comprises one or more databases adapted to provide claims processing, which involves the handling of pharmacy claims and managing of drug costs. The PBM servers 108 access formulary management databases that store and update the list of covered medications (formularies) for various insurance and other health benefit plans. The PBM server 108 receives the prescription data and transmits back to the switch server 104 approval or denial of the coverage for the prescription.

Prescription data generally includes insurance information, financial coverage information, such as Medicare Part D eligibility, patient information, and medication information. Patient information may include basic demographics such as the patient's name, date of birth, address, and contact information. It may also include allergies, medical history, and other relevant health data. Medication information may include drug name, both the brand and generic name of the medication; dosage information, such as the strength and amount of the medication prescribed; dosage form, such as tablets, capsules, liquids, etc.; directions on use; refills, date prescribed, and prescriber. Insurance information or financial coverage information may include the name of the patient's insurance company, financial plan, copay amount, etc.

The discount server 110 comprises computers, software, and applications that are implemented to take the medication and patient information and provide coverage in those scenarios where financial coverage was not provided by a plan, such as where the Medicare Part D plan did not provide coverage. In an embodiment, the discount server 110 implements coverage in scenarios where there is coverage, but the coverage provided by the discount server 110 is more cost effective.

Figure 2:
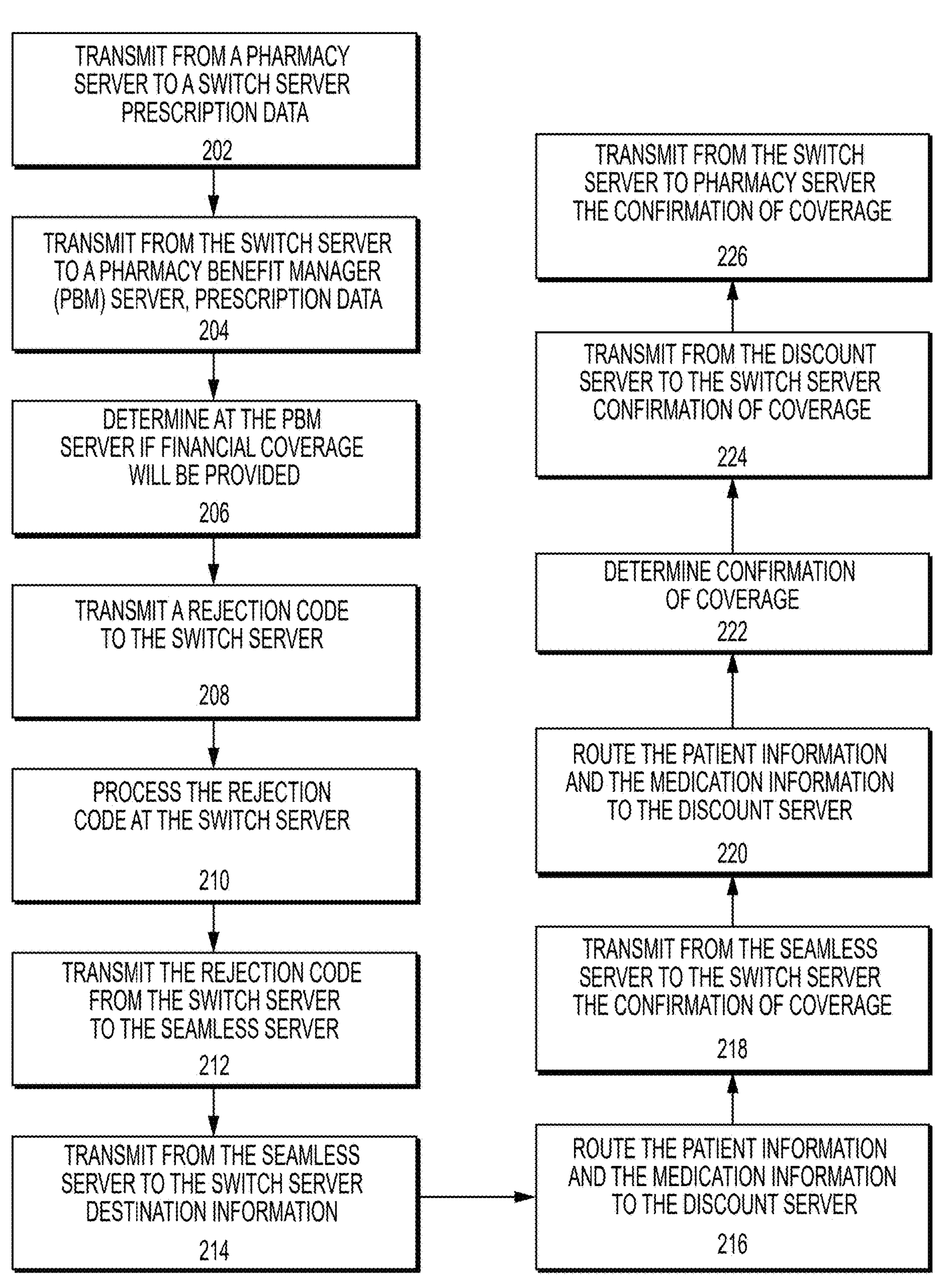
FIG. 2 shows a flow chart of the method for providing seamless discounted prescription pricing.

The general method for seamless provision of discount prescription information is shown in FIG. 2, with reference to those system components shown in FIG. 1. In step 202, prescription data is transmitted from the pharmacy server 102 to a switch server 104.

In step 204, the switch server 104 receives the prescription data and determines which PBM server 108 the prescription data is to be transmitted to. The switch server 104 then transmits the prescription data from the switch server 104 to the PBM server 108.

In step 206, the PBM server 108 processes the prescription data to determine if financial coverage will be provided by a plan, such as a Medicare Part D plan. PBM server 108 can do this based on information regarding plan coverage, such as Medicare coverage information, patient information, and the medication information.

In step 208, if the PBM server 108 determines that prescription service will not be provided, a rejection code is generated. The rejection code is then transmitted to the switch server 104.

In step 210, the switch server 104 processes the rejection code. The switch server 104, determines whether it meets criteria that is suitable for at least one discount server 110. In an embodiment, the rejection code meets predetermined claim rejection scenarios. These scenarios are for when to and when not to provide coverage for the requested medication. There are scenarios where the claims are denied, and they may be eligible for coverage through access to a discount server 110 and there are scenarios where claims are denied, and they will not be eligible for coverage through a discount server 110. Further, there are claims with multiple rejection codes attached to them that can still be eligible (e.g., a claim with a coverage denial rejection code may have other unrelated rejection codes that do not disqualify the claim from program eligibility). In an embodiment, having one rejection code that is non-qualifying may disqualify a claim from receiving coverage. In an embodiment, rejection codes may be weighted based on a combination of circumstances, with having more than one rejection exceeding a threshold value resulting in the total being non-qualifying. In an embodiment, rejection codes may disqualify a request if there are more rejection codes disqualifying a medication than qualifying a medication.

An approved transaction will be processed for a drug that is determined to be eligible by at least one discount server 110. In an embodiment, there may not be explicit limitations on which drugs qualify to be discounted, with exceptions for restricted drug categories identified in the non-eligible transaction section above. In an embodiment, eligible drugs for a program are defined by the GPIs (Generic Product Identifier) and/or NDCs (National Drug Code) provided by seamless server 106 to the switch server 104.

To determine if the rejection code corresponds to an actionable rejection code, the actionable code meets certain criteria, such as being a certain medication, having a certain cost, or the nature of the patient. An actionable rejection code is a code that the seamless server 106 can use to provide discount pricing by contacting the appropriate discount server 110.

Switch server 104 sends an application programming interface (API) call to seamless server 106 that includes relevant claim data for the seamless server 106 to determine which BIN/PCN/GroupID of a discount server 110 in the network of the seamless server 106 should be used to adjudicate the claim. Seamless server 106 will identify the correct BIN/PCN/GroupID of the discount server 110 and return this data to switch server 104. Switch server 104 will then use the identified BIN/PCN/GroupID of the discount server 110 and send that claim to that destination for use by the discount server 110.

In step 212, the switch server 104 transmits the rejection code to the seamless server 106 based on the processing of the rejection code. This overrides the standard process of sending the rejection code directly to the pharmacy server 102. Thus, the seamless server 106 operates on top of the existing prescription dispensation network to seamlessly provide discounts and coverage when the existing financial coverage is denied.

In step 214, the seamless server 106 transmits from the seamless server 106 to the switch server 104 destination information that the switch server 104 then uses to transmit patient information and medication information. The destination information is the information needed to transmit the data to the discount server 110.

In step 216, the switch server 104 transmits the patient and medication information to the discount server 110. In step 218, the discount server 110 determines coverage using the patient and medication information. In step 220, the discount server 110 transmits from the discount server 110 to the switch server 104 confirmation of coverage.

If switch server 104 receives a response from the BIN/PCN/GroupID of discount server 110 identified by seamless server 106, the claim will be passed back to the pharmacy server 102 containing the cash price option and seamless server 106 will notify the patient's benefit plan of the cash price transaction.

If switch server 104 receives a rejected response from the BIN/PCN/GroupID of discount server 110 identified by seamless server 106, switch server 104 will pass the original claim rejection message from the PBM server 108 back to the pharmacy server 102.

If switch server 104 receives a claim reversal transaction from a pharmacy server 102 that received the cash pricing option from the CDC BIN/PCN/GroupID identified by seamless server 106, switch server 104 will send the claim reversal to seamless server 106 using the BIN/PCN/GroupID of the discount server 110 provided by seamless server 106 and seamless server 106 will notify the PBM server 108 of the reversal.

In step 222, the switch server 104 transmits confirmation of coverage to the pharmacy server 102.

Figure 3:
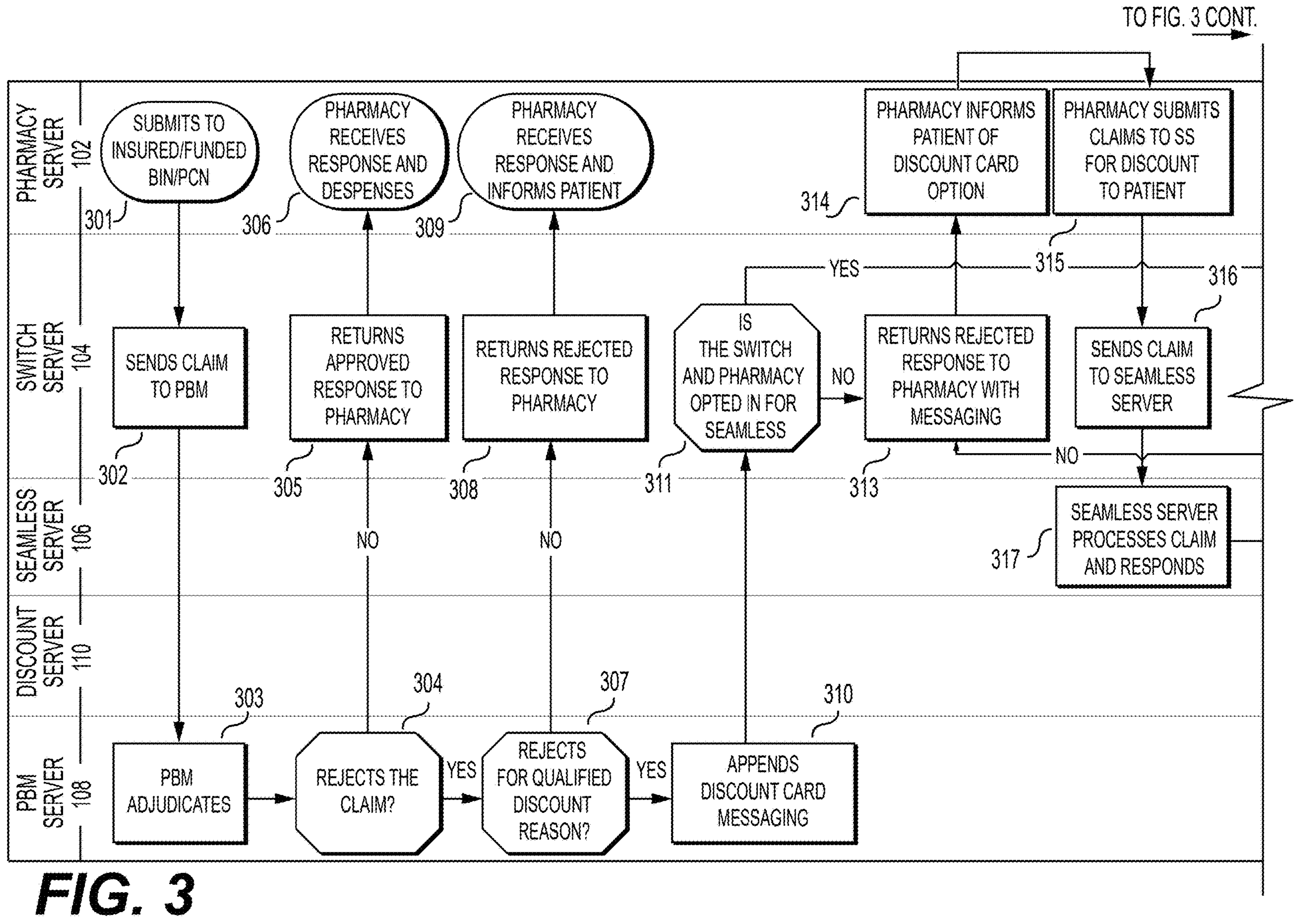
FIG. 3 shows a chart of the system operation.
Figure 3:
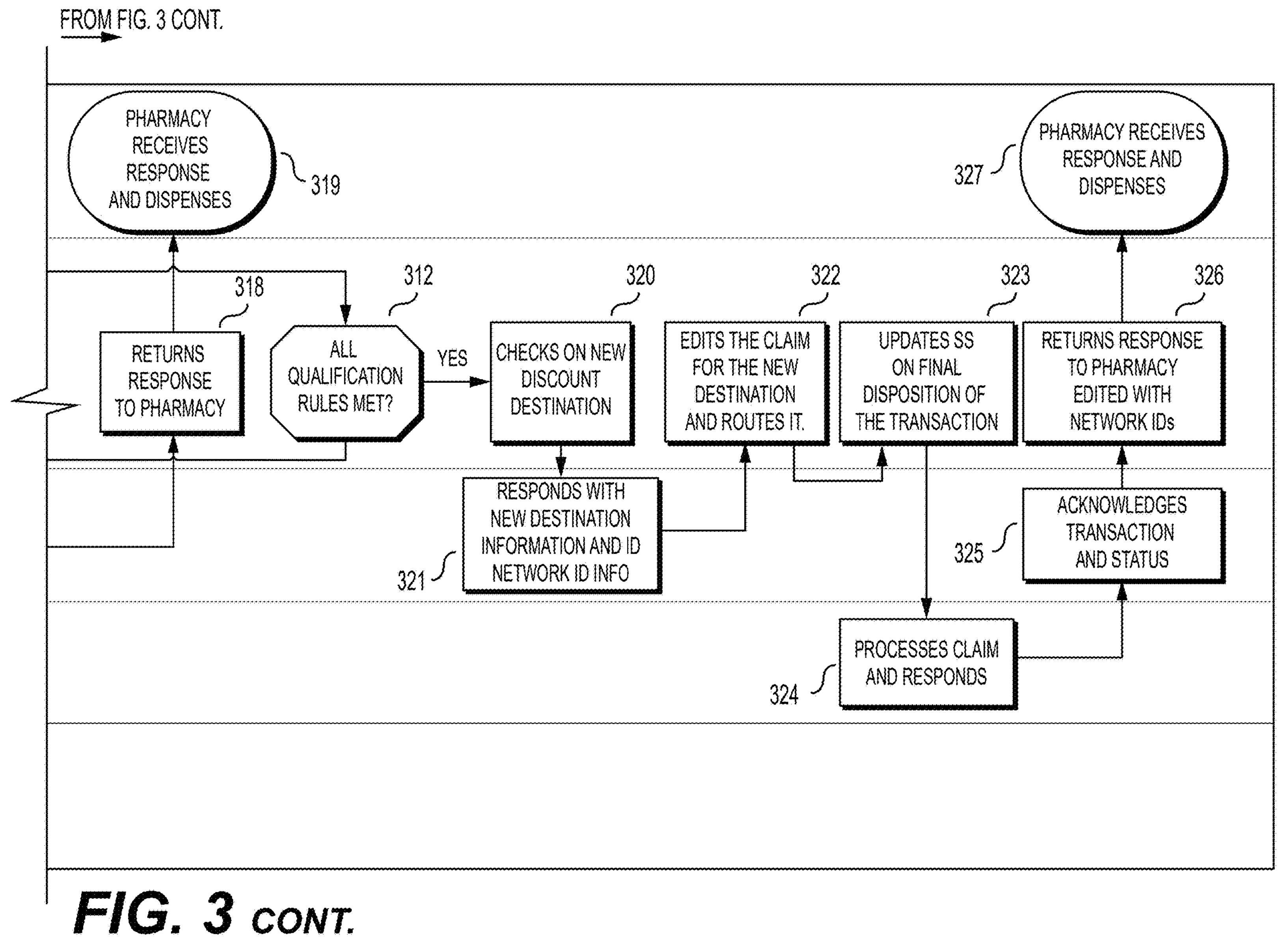

Now referring to FIG. 3, with reference to FIG. 1, shown is a chart of the system operation and the decision chart of the submission of a prescription. The chart shows the decisions and steps made at the pharmacy server 102, switch server 104, seamless server 106, discount server 110, and PBM server 108.

At step 301, the prescription data is submitted to the pharmacy server 102. This information can include insured, funded, bank identification number (BIN) and processor control number (PCN). The prescription data is sent to the switch server 104. At step 302, the prescription data is sent from the switch server 106 to the PBM server 108.

In step 303, the PBM server 108 adjudicates the prescription data. By adjudicating the prescription data, it is meant that it is determined whether the prescription data provides information that would generate a positive coverage response.

In step 304, it is determined if the claim is rejected or accepted. Acceptance or rejection of claim is based on the information contained in the prescription data. If the claim is accepted, the PBM server 108 sends this information to the switch server 104.

In step 305, the switch server 104 transmits the approval of the claim to the pharmacy server 102. In step 306, the prescription based on the prescription data will be dispensed.

If the claim is denied, at step 307 the reason for the denial is determined, rejection codes are generated and then sent to switch server 104. If the switch server 104 determines that the rejection code does not meet the criteria for at least one discount server 110, at step 308 the denial of claim is transmitted to the pharmacy server 102. At step 309, the pharmacy informs the patient that there will be no coverage.

If at step 307, the rejection code was generated for a reason that discount prescription services will cover, that information is noted in the rejection code at step 310. At step 311, the switch server 104 determines if the pharmacy server 102 that submitted the prescription data is part of the seamless server network. The seamless server network is that system of discount servers 110 that can intervene when the prescription data causes PBM server 108 to generate rejection codes that are actionable by the discount servers 110. If the pharmacy server 102 is not part of the seamless server network, at step 313, the rejection is sent to the pharmacy server 102 along with messaging. At step 314 the pharmacy can provide information about discount options to the patient.

At step 315, the pharmacy server 102 can send the prescription data from the pharmacy server 102 to the switch server 104. At step 316, the switch server 104 sends the claim data to the seamless servers 106. At step 317 the seamless server 106 processes the claims and responds by transmitting the response to the switch server 104. At step 318 the switch server 104 transmits the response to the pharmacy server 102. At step 319 the response is received at the pharmacy server 102 and the prescription is dispensed to the patient.

If the pharmacy server 102 is part of the seamless server network, at step 312 it will be determined if the qualifications are met. If the qualifications are not met, then steps 313-319 are followed. If the qualifications are met, then at step 320, the switch server 104 sends a request to the seamless server 106 to determine the discount server 110 destination. At step 321 the seamless server 106 provides the destination of the discount server 110. At step 322 the claim is edited to provide the destination for the discount server 110. At step 323 the switch server 104 updates the seamless server 106 on the final disposition of the transaction. At step 324 the discount server 110 transmits to the seamless server 106 acknowledgment of the transaction and the status. In step 326, the switch server 104 returns the response to the pharmacy server 102 with the IDs of the discount servers 110. In step 327, the pharmacy dispenses the medication to the patient.

The seamless prescription discounting (SPD) system 100 comprises the PBM server, pharmacy server, switch server, seamless server, and discount server communicating the above-described data, and may exist in a separate server, and/or in software enhancements to the PBM server, Pharmacy Server, Seamless server, switch Server, and discount Server, or otherwise.

Wherever possible, the same or like reference numbers are used throughout the drawings to refer to the same or like features. It should be noted that the drawings are in simplified schematic form and are not drawn to precise scale. Certain terminology used in the description is for convenience only and is not limiting. For example, directional terms such as top, bottom, left, right, above, below and diagonal, are used with respect to the accompanying drawings. The words "inwardly" and "outwardly" refer to directions toward and away from, respectively, the geometric center of the identified element and designated parts thereof. Such directional terms used in conjunction with the following description of the drawings should not be construed to limit the scope of the present disclosure in any manner not explicitly set forth. Additionally, the term "a," as used in the specification, means "at least one." The terminology includes the words above specifically mentioned, derivatives thereof, and words of similar import.

"Substantially" as used herein shall mean considerable in extent, largely but not wholly that which is specified, or an appropriate variation therefrom as is acceptable within the field of art. "Exemplary" as used herein shall mean serving as an example.

"About" as used herein when referring to a measurable value such as an amount, a temporal duration, and the like, is meant to encompass variations of ±20%, ±10%, ±5%, ±1%, or ±0.1% from the specified value, as such variations are appropriate.

Throughout this disclosure, various embodiments of the present invention can be presented in a range format. It should be understood that the description in range format is merely for convenience and brevity and should not be construed as an inflexible limitation on the scope of the present invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of exemplary embodiments may be combined in any suitable manner in one or more embodiments. One skilled in the art will recognize, in light of the description herein, that the exemplary embodiments can be practiced without one or more of the specific features or advantages of a particular embodiment. In other instances, additional features and advantages may be recognized in certain embodiments that may not be present in all embodiments of the present disclosure.

While the disclosure is described herein, using a limited number of embodiments, these specific embodiments are not intended to limit the scope of the disclosure as otherwise described and claimed herein. The precise arrangement of various elements and order of the steps of articles and methods described herein are not to be considered limiting. For instance, although the steps of the methods are described with reference to sequential series of reference signs and progression of the blocks in the figures, the method can be implemented in any order as desired.

The invention claimed is:

1. A method for seamless provision of discount prescription information executed by a networked claims processing system comprising a pharmacy server, a switch server, a seamless server, and at least one discount server, comprising:

transmitting prescription data from a pharmacy server to a switch server;

transmitting the prescription data from the switch server to a pharmacy benefit manager (PBM) server;

determining at the PBM server if financial coverage will be provided based on the prescription data;

transmitting a rejection code to the switch server if it is determined that coverage will not be provided;

at the switch server, computing an eligibility score from a plurality of rejection codes by applying a weighting model that assigns different weights to respective rejection codes and comparing a sum of the weights to a threshold, and processing the plurality of rejection codes at the switch server to determine if the plurality of rejection codes corresponds to an actionable claim;

responsive to the eligibility score satisfying the threshold, generating by the switch server, an edited claim that replaces original routing fields with destination information for sending the patient information and the medication information, wherein the destination information is at least one discount server, the destination information comprising a BIN, a PCN, and a GroupID identified by the seamless server;

invoking, by the switch server, an application programming interface (API) of the seamless server with at least the plurality of rejection codes, GPI and/or NDC of the medication, and cost parameters;

receiving, from the seamless server, the BIN/PCN/GroupID associated with a discount server selected according to a deterministic selection policy that prioritizes lowest cash price and, when prices are equal, applies a server-specific rank;

routing the patient information and the medication information using the edited claim to the selected discount server without user re-entry of the prescription data;

determining confirmation of coverage at the discount server using the patient information and the medication information;

transmitting from the discount server to the switch server confirmation of coverage; and transmitting from the switch server to the pharmacy server the confirmation of coverage, wherein the transmitting includes updating a transaction state at the seamless server and notifying the PBM server of cash-price adjudication or reversal, thereby reducing repeated network round-trips and resubmissions.

2. The method of claim 1, wherein there is more than one discount server.

3. The method of claim 2, wherein computing the eligibility score comprises summing weights to rejection codes and comparing the sum to a threshold to determine actionability.

4. The method of claim 1, wherein at least one of the plurality of rejection codes is determined based on the medication information.

5. The method of claim 1, wherein wherein not all of the plurality of rejection codes are transmitted to the seamless server.

6. The method of claim 1, wherein the prescription data comprises financial coverage information, patient information, and medication information.

7. The method of claim 1, wherein a claim reversal is sent to the seamless server and the PBM server is notified of the claim reversal.

8. The method of claim 1, further comprising transmitting confirmation of coverage to the seamless server in addition to transmitting confirmation of coverage to the switch server.

9. The method of claim 1, wherein more than one rejection code is generated for the prescription data.

10. The method of claim 9, wherein each of the more than one rejection code is determined to be actionable by the discount server.

11. A system for seamless provision of discount prescription information comprising:

a pharmacy server adapted to receive and transmit prescription data;

a switch server operably connected to the pharmacy server, wherein the switch server is adapted to receive and transmit prescription data and configured to: (i) parse a plurality of rejection codes returned by a PBM server; (ii) compute an eligibility score by applying code-specific weights; (iii) compare the eligibility score to a threshold; and (iv) when the threshold is satisfied, generate an edited claim with a BIN/PCN/GroupID selected by a seamless server;

a pharmacy benefit manager (PBM) server adapted to receive prescription data and generate a rejection code set based in part on the prescription data;

a seamless server adapted to receive processed rejection codes and GPI and/or NDC identifiers from the switch server and processed by the switch server and based on a deterministic selection policy that prioritizes lowest cash price and applies server-specific rank for tie-breaking return destination data comprising a BIN/PCN/GroupID of a discount server;

a discount server adapted to provide confirmation of coverage to the switch server and to provide transaction acknowledgments to the seamless server to the PBM server during cash-price transactions and reversals, thereby reducing re-keying at the pharmacy server and decreasing adjudication latency.

12. The system of claim 11, wherein computing the eligibility score comprises summing weights to rejection codes and comparing the sum to a threshold to determine actionability.

13. The system of claim 12, wherein the seamless server is adapted to process the rejection code to determine which discount server to provide destination information to.

14. The system of claim 13, wherein at least one of the rejection codes is determined based on the medication information.

15. The system of claim 11, wherein not all rejection codes are transmitted to the seamless server.

16. The system of claim 11, wherein the prescription data comprises financial coverage information, patient information, and medication information.

17. The system of claim 11, wherein the pharmacy server is cloud-based.

18. The system of claim 11, wherein the discount server is adapted to provide confirmation of coverage to the seamless server in addition to the switch server.

19. The system of claim 18, wherein more than one rejection code is generated for the prescription data.

20. The system of claim 19, wherein each of the more than one rejection code is determined to be actionable by the discount server.

* * * * *